(12) United States Patent
Faure et al.

(10) Patent No.: US 7,125,558 B2
(45) Date of Patent: Oct. 24, 2006

(54) PROCESS FOR THE PREPARATION OF ACTIVATED POLYETHYLENE GLYCOLS

(75) Inventors: Marie-Pierre Faure, Ville St-Laurent (CA); Micheal Ibea, Montreal (CA)

(73) Assignee: Bioartificial Gel Technologies Inc,, Montreal (CA)

( * ) Notice: Subject to any disclaimer, the term of this patent is extended or adjusted under 35 U.S.C. 154(b) by 253 days.

(21) Appl. No.: 10/487,392

(22) PCT Filed: Aug. 22, 2002

(86) PCT No.: PCT/CA02/01306

§ 371 (c)(1), (2), (4) Date: Feb. 20, 2004

(87) PCT Pub. No.: WO03/018665

PCT Pub. Date: Mar. 6, 2003

(65) Prior Publication Data

US 2005/0080206 A1     Apr. 14, 2005

Related U.S. Application Data

(60) Provisional application No. 60/313,801, filed on Aug. 22, 2001.

(51) Int. Cl.
*A61K 9/00*      (2006.01)
*C08G 64/00*    (2006.01)

(52) U.S. Cl. .................. 424/400; 528/196; 528/198

(58) Field of Classification Search ............... 528/196, 528/198; 424/400
See application file for complete search history.

(56) References Cited

U.S. PATENT DOCUMENTS

| | | | |
|---|---|---|---|
| 3,463,862 A | 8/1969 | Mazza | 523/103 |
| 4,002,531 A | 1/1977 | Royer | 195/68 |
| 4,101,380 A | 7/1978 | Rubinstein et al. | 195/63 |
| 4,161,948 A | 7/1979 | Bichon | 128/156 |
| 4,179,337 A | 12/1979 | Davis et al. | 435/181 |
| 4,264,155 A | 4/1981 | Miyata | 351/160 H |
| 4,388,428 A | 6/1983 | Kuzma et al. | 523/106 |
| 4,464,468 A | 8/1984 | Avrameas et al. | 435/177 |
| 4,650,616 A | 3/1987 | Wajs | 264/2.6 |
| 4,752,627 A | 6/1988 | Froix | 523/106 |
| 4,791,192 A | 12/1988 | Nakagawa et al. | 530/399 |
| 4,879,072 A | 11/1989 | Bourset et al. | 264/1.4 |
| 5,039,540 A | 8/1991 | Ecanow | 426/385 |
| 5,051,406 A | 9/1991 | Satoh | 514/21 |
| 5,079,018 A | 1/1992 | Ecanow | 426/385 |
| 5,114,627 A | 5/1992 | Civerchia | 264/1.1 |
| 5,122,614 A | 6/1992 | Zalipsky | 548/520 |
| RE33,997 E | 7/1992 | Kuzma et al. | 523/106 |
| 5,183,660 A | 2/1993 | Ikeda et al. | 424/94.3 |
| 5,185,368 A | 2/1993 | Peter et al. | 514/476 |
| 5,214,131 A | 5/1993 | Sano et al. | 530/345 |
| 5,229,366 A | 7/1993 | Tsukada et al. | 514/12 |
| 5,235,028 A | 8/1993 | Barany et al. | 528/335 |
| 5,252,714 A | 10/1993 | Harris et al. | 530/391.9 |
| 5,281,698 A | 1/1994 | Nitecki | 530/351 |
| 5,286,637 A | 2/1994 | Veronese et al. | 435/183 |
| 5,298,410 A | 3/1994 | Phillips et al. | 435/188 |
| 5,298,643 A | 3/1994 | Greenwald | 558/6 |
| 5,321,095 A | 6/1994 | Greenwald | 525/404 |
| 5,324,844 A | 6/1994 | Zalipsky | 548/520 |
| 5,334,382 A | 8/1994 | Phillips et al. | 424/94.3 |
| 5,342,940 A | 8/1994 | Ono et al. | 544/218 |
| 5,349,001 A | 9/1994 | Greenwald et al. | 525/408 |
| 5,382,657 A | 1/1995 | Karasiewicz et al. | 530/351 |
| 5,389,381 A | 2/1995 | Phillips et al. | 424/94.3 |
| 5,405,877 A | 4/1995 | Greenwald et al. | 514/772.3 |
| 5,446,090 A | 8/1995 | Harris | 525/54.1 |
| 5,650,234 A | 11/1995 | Saifer et al. | 424/78.27 |
| 5,514,572 A | 5/1996 | Veronese et al. | 435/180 |
| 5,529,915 A | 6/1996 | Phillips et al. | 435/188 |
| 5,539,063 A | 7/1996 | Hakimi et al. | 525/403 |
| 5,545,698 A | 8/1996 | Barany et al. | 525/420 |
| 5,556,948 A | 9/1996 | Tagawa et al. | 530/391.9 |
| 5,559,213 A | 9/1996 | Hakimi et al. | 530/351 |
| 5,567,422 A | 10/1996 | Greenwald | 424/78.3 |
| 5,595,732 A | 1/1997 | Hakini et al. | 424/85.7 |
| 5,605,976 A | 2/1997 | Martinez et al. | 525/408 |
| 5,637,749 A | 6/1997 | Greenwald | 558/6 |
| 5,681,567 A | 10/1997 | Martinez et al. | 424/178.1 |
| 5,733,563 A | 3/1998 | Fortier | 424/422 |
| 5,747,646 A | 5/1998 | Hakimi et al. | 530/351 |
| 5,792,834 A | 8/1998 | Hakimi et al. | 530/351 |
| 5,834,594 A | 11/1998 | Hakimi et al. | 530/351 |

(Continued)

FOREIGN PATENT DOCUMENTS

CA    2331139    11/1999

(Continued)

OTHER PUBLICATIONS

International Search Report for International Application Serial No. PCT/CA02/01306, dated Dec. 23, 2002, 4 pages.

(Continued)

*Primary Examiner*—Kamal A. Saeed
*Assistant Examiner*—Susannah L. Chung
(74) *Attorney, Agent, or Firm*—Kirkpatrick & Lockhart Nicholson Graham LLP

(57) ABSTRACT

The present invention relates to a process for the preparation of activated polyethylene glycols, or PEG(NPC)$^2$s, comprising reacting polyethylene glycol with an activator while in the presence of an aromatic nitrogen containing heterocyclic base. The process is carried out at temperatures ranging from about 20 to about 30° C., more preferably at room temperature, and under stoichiometric conditions.

23 Claims, 3 Drawing Sheets

U.S. PATENT DOCUMENTS

| | | | | |
|---|---|---|---|---|
| 5,849,860 | A | 12/1998 | Hakimi et al. | 528/370 |
| 5,900,461 | A | 5/1999 | Harris | 525/54.11 |
| 5,932,462 | A | 8/1999 | Harris et al. | 435/188 |
| 5,973,069 | A | 10/1999 | Kataoka et al. | 525/54.2 |
| 6,214,966 | B1 | 4/2001 | Harris | 528/322 |
| 6,348,558 | B1* | 2/2002 | Harris et al. | 528/196 |
| 6,515,100 | B1 | 2/2003 | Harris | 528/322 |
| 6,773,703 | B1 | 8/2004 | Ettner et al. | 424/94.1 |
| 2003/0083389 | A1* | 5/2003 | Kao et al. | 516/98 |
| 2004/0082716 | A1 | 4/2004 | Faure et al. | 525/54.1 |

FOREIGN PATENT DOCUMENTS

| | | |
|---|---|---|
| EP | 0 648 742 | 1/1997 |
| EP | 1 055 685 | 11/2000 |
| EP | 0 705 298 | 3/2002 |
| WO | WO 01/74928 | 10/2001 |
| WO | WO 02/070590 | 9/2002 |
| WO | WO 03/018665 | 3/2003 |

OTHER PUBLICATIONS

Fortier, G. et al. (1993), "Surface modification of horseradish peroxidase with poly(ethylene glycol)s of various molecular masses," *Biotechnol. Appl. Biochem.*, vol. 17, pp. 115-130.

Hai, T.T. et al. (1999), "Polymerization of Diaspirin Crosslinked Hemoglobin (DCLHb) with PEG Activated with Benzenesulfonate Bearing Electron-Withdrawing Groups," *Tetrahedron*, vol. 55, pp. 2147-2156.

Mehvar, R. (2000), "Modulation of the Pharmacokinetics and Pharmacodynamics of Proteins by Polyethylene Glycol Conjugation," *J. Pharm. Pharmaceut. Sci.*, vol. 3, No. 1, pp. 125-136.

Morpurgo, M. et al. (1996), "Preparation and Characterization of Poly(ethylene glycol) Vinyl Sulfone," *Bioconjugate Chem.*, vol. 7, pp. 363-368.

Roberts, M.J. et al. (2002), "Chemistry for peptide and protein PEGylation," *Advanced Drug Delivery Reviews*, vol. 54, pp. 459-476.

D'Urso, E.M. et al. (1994), "New Bioartificial Polymeric Material: Poly(ethylene glycol) Cross-Linked with Albumin. I. Synthesis and Swelling Properties," vol. 9, pp. 367-387.

Sartore et al. (1991), "Enxyme Modification by MPEG with an Amino Acid Peptide as Spacer Arms," *Appl. Biochem. Biotechnol.*, vol. 27, pp. 45-54.

Anderson, W.L. et al., "Polymer modification of antibody to eliminate immune complex and Fc binding," *Journal of Immunology Methods*, 109(1):37-42 (1988).

Beuchamp, C.O. et al., "A New Procedure for the Synthesis of Polyethylene Glycol-Protein Adducts; Effects on Function, Receptor Recognition, and Clearance of Superoxide Dismutase, Lactoferrin, and $\beta_2$-Macroglobulin," *Analytical Biochemistry*, 131(1):25-33 (1983).

Delgado, C. et al., "Coupling of Poly(ethylene glycol) to Albumin under Very Mild Conditions by Activation with Tresyl Chloride: Characterization of the Conjugate by Partioning in Aqueous Two-Phase Systems," *Biotechnology and Applied Biochemistry*, 12:119-128 (1990).

Nishimura, H. et al., "Modification of Batroxobin with Activated Polyethylene Glycol: Reduction of Binding Ability Towards Anti-Batroxobin Antibody and Retention of Defibrinogenation Activity in Circulation of Preimmunized Dogs," *Life Sciences*, 33:1467-1473 (1983).

Veronese, F.M. et al., "Surface Modification of Proteins, Activation of Monomethoxy-Polyethylene Glycols by Phenylchloroformates and Modification of Ribonuclease and Superoxide Dismutase," *Applied Biochemistry and Biotechnology*, 11(2):141-152 (1985).

Wirth, P. et al., "Chemical Modification of Horseradish Peroxidase with Ethanal-Methoxypolyethylene Glycol: Solubility in Organic Solvents, Activity, and Properties," *Bioorganic Chmeistry*, 19(2):133-142 (1991).

Zaplisky, S. et al., "Facile Synthesis of $\alpha$-Hydroxy-$\chi$-Carboxymethylpolyethylene Oxide," *Journal of Bioactive and Compatible Polymers*, 5(2):227-231 (1990).

Zaplisky, S., "Functionalized Poly(ethylene glycol) for Preparation of Biologically Relevant Conjugates," *Bioconjugate Chemistry*, 6:150-165 (1995).

* cited by examiner

PROCESS FOR THE PREPARATION OF ACTIVATED POLYETHYLENE GLYCOLS

CROSS-REFERENCE TO RELATED APPLICATIONS

This application is the national phase under 35 U.S.C. § 371 of International Application No. PCT/CA02/01306, filed Aug. 22, 2002, published under PCT Article 21(2) in English, which claims priority to and the benefit of U.S. Provisional Patent Application No. 60/313,801, filed Aug. 22, 2001, the disclosures of which are incorporated by reference herein.

FIELD OF THE INVENTION

The present invention relates to a process for the rapid preparation of activated polyethylene glycols, or PEG(NPC)$_2$s. More specifically, the present invention is concerned with a process for the preparation of activated PEGs involving shorter reaction times, lower reaction temperatures and allowing for the expeditious recovery of the activated PEGs by a simple extraction procedure. Additionally, the present invention relates to a process for the preparation of activated PEGs wherein stoichiometric amounts of reagents are used. The invention further covers the activated PEGs produced by this rapid process and their use in a variety of pharmaceutical, medical, cosmetical and chemical applications.

BACKGROUND OF THE INVENTION

Polyethylene glycol (PEG) is a polymer having the structure $H(O-CH_2CH_2-)_nOH$. It is generally synthesized by the ring opening polymerization of ethylene oxide. While the polymer usually has a linear structure at molecular weights $\leq 10$ kD, the higher molecular weight PEGs may have some degree of branching.[1] Polyethylene glycols of different molecular weights have previously been used in a number of applications, including to increase the solubility of drugs. During the last three decades, polyethylene glycol has been extensively investigated for delivery of various proteins via parenteral routes. Generally, PEGs have been most widely used for the delivery of both traditional drugs (small molecules) and proteins/enzymes in the treatment of cancer.

Several chemical procedures have been developed for the preparation of activated PEGs, which can then be used to react specifically with free amino groups on an enzyme's surface, under mild aqueous conditions. PEGs have been successfully activated by reaction with 1,1-carbonyl-di-imidazole, cyanuric chloride, tresyl chloride, 2,4,5-trichlorophenyl chloroformate or 4-nitrophenyl chloroformate, various N-hydroxy-succinimide derivatives as well as by the Moffatt-Swern reaction.[2-10] In most cases, the activating agent acts as a linker between the PEG and the enzyme or protein.

One of the major disadvantages encountered with the processes currently available involves the reaction temperatures at which the activation reactions are carried out. The most commonly used solvents are acetonitrile ($CH_3CN$) and dichloromethane ($CH_2Cl_2$), containing small volumes of a co-solvent, usually triethylamine (TEA). Usually, the activation reactions are carried out under refluxing conditions at a temperature of about 84° C. when acetonitrile is used, or at a temperature of about 40° C. when dichloromethane is chosen as the solvent.

Several crystallization steps are commonly required for the isolation and purification of the activated PEG product. Such steps can make currently available processes for the activation of PEGs inconvenient.

The activation of PEGs with 4-nitrophenyl chloroformate, to generate PEG-di-nitrophenyl carbonates, has been described by Fortier and Laliberté.[10] The reactions were carried out in acetonitrile containing triethylamine (TEA) over a period of 5 hours at 60° C. The long reaction times and the reaction temperatures required to perform the activation reactions are major disadvantages of this process. Additionally, in order to keep the system as anhydrous as possible, the use of a cumbersome soxhlet is required. This imparts a severe limitation on the activation process, especially when transposed on a larger scale.

There is thus a need for a low-cost process for the activation of PEGs that is time efficient and that can be performed at room temperature. There is also a need for a process allowing for the rapid isolation and purification of the activated PEGs.

Moreover, there is a need for a process for PEG activation that is amenable to large-scale production.

The present invention seeks to meet these and other needs.

SUMMARY OF THE INVENTION

The present invention relates to a novel process for the activation of PEGs that is characterized by improved reaction efficiency and improved reaction conditions.

The present invention relates to a novel process for the activation of PEGs that is characterized by the use of stoichiometric amounts of reagents and that provides a very high degree of activation.

The present invention also relates to a novel process for the activation of PEGs that is further characterized by low manufacturing costs and that is easily amenable to large scale production.

In addition, the present invention relates to a novel process for the isolation and purification of the produced activated PEGs, characterized by an efficient extraction and precipitation procedure.

According to one aspect of the present invention, there is provided a process for preparing activated polyethylene glycols (PEGs), comprising reacting polyethylene glycol (PEG) with an activator in the presence of an aromatic nitrogen-containing heterocyclic base, wherein the activator has the general structure Y-Q-X and may be selected from, but is not limited to, the group consisting of $ClSO_2Cl$, $ClCOCH_2SO_2Cl$, $4-O_2NPhOCOCl$, $2-O_2NPhOCOCl$, $PhO-COCl$, $ClSO_2CH_2CH_2SO_2Cl$, $POCl_3$, $PhOPOCl_2$, $PhPOCl_2$, $CCl_3COCl$, $CBr_3COCl$, and $X_bPhOCOCl$ wherein X and Y may be identical or different and represent an electron withdrawing group, and wherein "b" is an integer ranging from 1 to 3.

Unless defined otherwise, the scientific arid technological terms and nomenclature used herein have the same meaning as commonly understood by a person of ordinary skill. Generally, procedures such as extraction, precipitation and recrystallization are common methods used in the art. Such standard techniques can be found in reference manuals such as for example Gordon and Ford (The Chemist's Companion: A handbook of Practical Data, Techniques and References, John Wiley & Sons, New York, N.Y., 1972).

The present description refers to a number or routinely used chemical terms. Nevertheless, definitions of selected terms are provided for clarity and consistency.

As used herein, the expression "aprotic solvent", refers to a solvent that does not possess an acidic proton.

As used herein, the expression "electron withdrawing group", refers to a substituent on an aromatic ring that withdraws electrons from the aromatic ring by inductive effects and/or by resonance effects.

As used herein, the term "about" refers to a +/−5% variation from the nominal value.

As used herein, the formula PEG(NPC)$^2$, refers to a polyethyleneglycol, bis activated with a 4-Nitro-Phenyl Carbonate group.

Further scope of applicability will become apparent from the detailed description given hereinafter. It should be understood, however, that this detailed description, while indicating preferred embodiments of the invention, is given by way of illustration only, since various changes and modifications will become apparent to those skilled in the art.

DETAILED DESCRIPTION OF THE INVENTION

Figure 1:
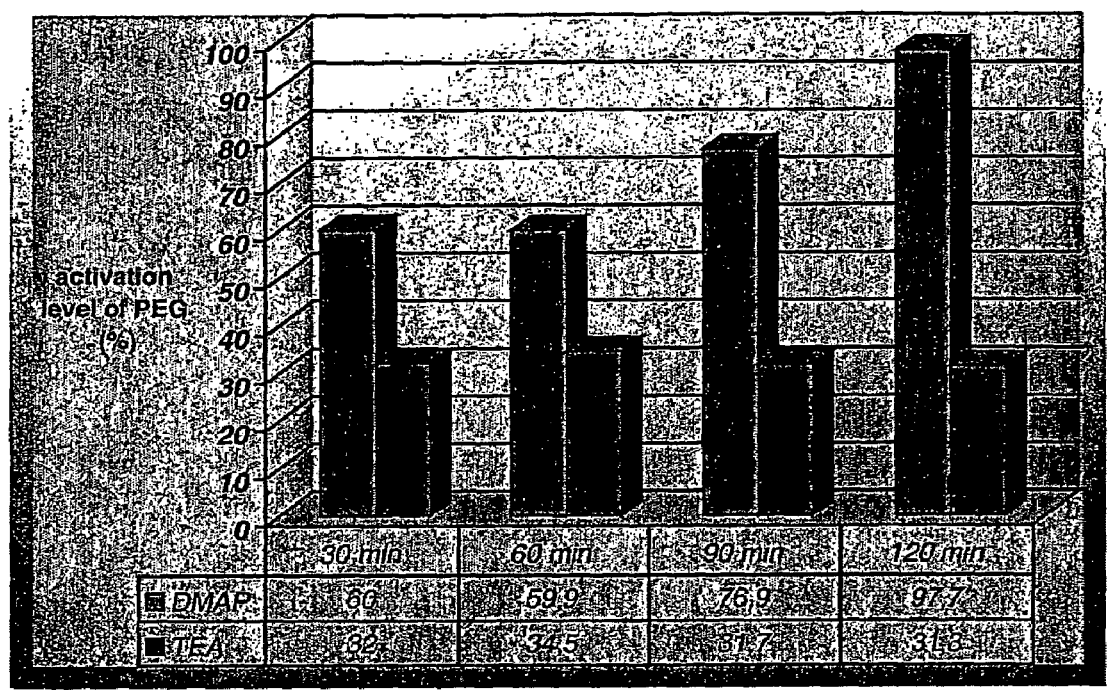
FIG. 1 represents a block diagram depicting the degree of PEG activation in processes using DMAP and TEA respectively, with 4-nitrophenyl chloroformate as the activator, and using stoichiometric amounts of all reagents. The activation reactions were carried out in $CH_2Cl_2$ at room temperature.
Figure 2:
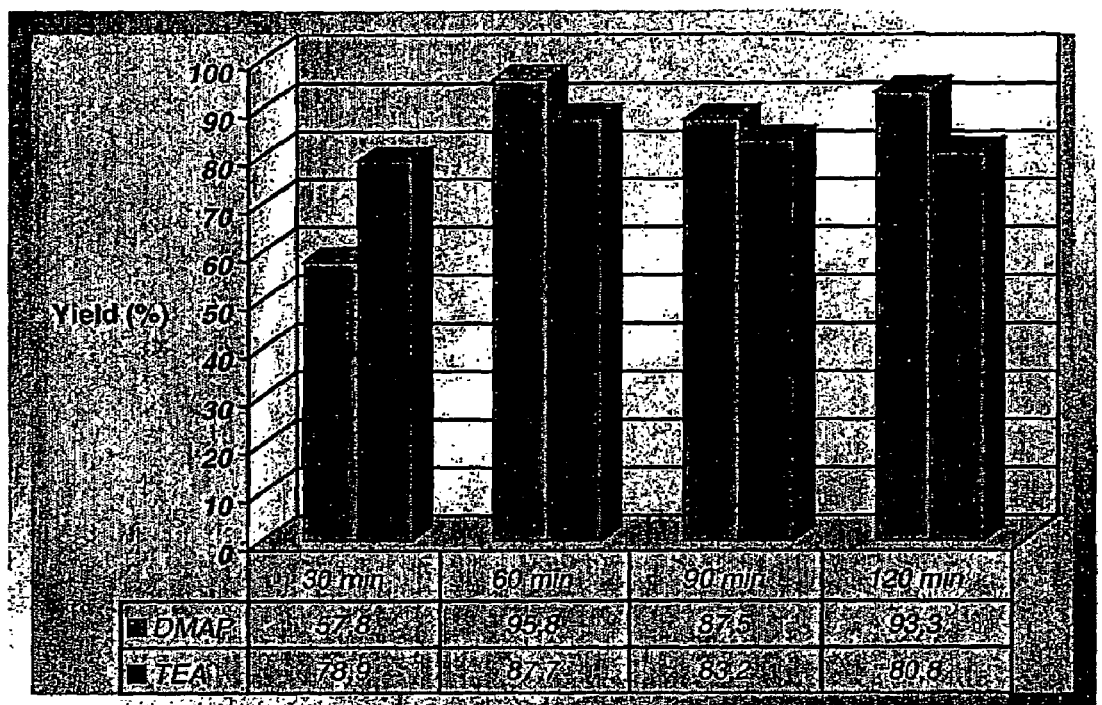
FIG. 2 represents a block diagram depicting the yields of activated PEG produced by both the DMAP and the TEA processes using 4-nitrophenyl chloroformate as the activator and using stoichiometric amounts of all reagents. The activation reactions were carried out in $CH_2Cl_2$ at room temperature.
Figure 3:
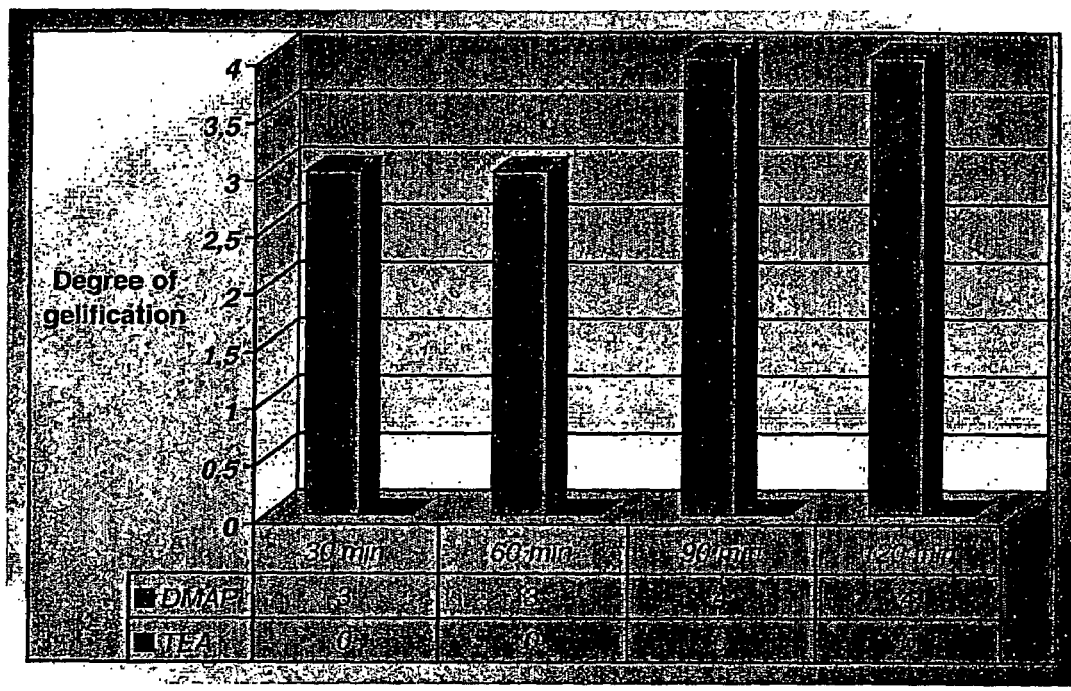
FIG. 3 represents a block diagram depicting the degree of gelification of the activated PEGs produced by both the DMAP and TEA procedures using 4-nitrophenyl chloroformate as the activator and using stoichiometric amounts of all the reagents. The activation reactions were carried out in $CH_2Cl_2$ at room temperature.

In a broad sense, the present invention provides a novel process for the activation of PEGs that is characterized by improved reaction times and reaction conditions, and that is easily amenable to large scale production while maintaining low manufacturing costs.

The activation of PEG using various activating agents while in the presence of an aromatic nitrogen containing heterocyclic base, more specifically dimethylaminopyridine (DMAP), was investigated. The activation reactions were carried out in an aprotic solvent system, preferably composed of methylene chloride ($CH_2Cl_2$). The activation reactions were carried out using stoichiometric amounts of PEG, an activating agent such as 4-nitrophenyl chloroformate, and 4-DMAP, and were performed at temperatures ranging from about 20 to about 30° C. and more preferably at room temperature.

The aprotic solvent used in the present invention is selected from the group consisting of DMSO, DMF, acetonitrile, nitromethane, HMPA, acetone, acetic anhydride, pyridine, o-dichlorobenzene, chlorobenzene, benzene, toluene, xylene, methylene chloride, carbon tetrachloride, THF, dioxane, ethyl acetate, DME, and carbon disulfide. These aprotic solvents have a boiling point ranging from about 35° C. to about 230° C.

The only significant side product generated in the activation process, is the hydrochloric acid salt of DMAP. This salt can be efficiently removed from the reaction mixture by simple extraction and filtration procedures. This straightforward purification procedure allows for the isolation of a very pure activated PEG product. Note that while the reaction is carried out under stoichiometric conditions, any unreacted reagent can also removed from the reaction mixture by the above mentioned purification procedures.

The PEG activation process of the present invention can be adequately described by the following general reaction sequence:

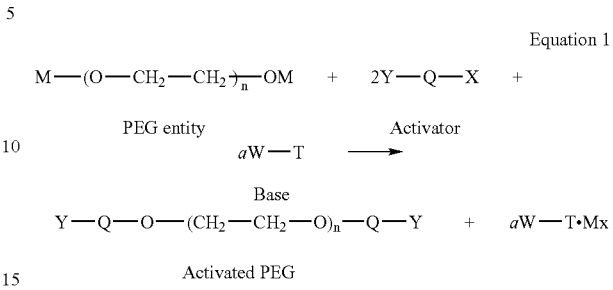

Equation 1

Activated PEG wherein M represents a hydrogen atom or an atom selected from the group consisting of Li, Na, K, Rb, and Cs and wherein "a" is an integer preferably ranging from 0 to 6 and more preferably ranging from 0 to 2.

The activator Y-Q-X is capable of the in situ generation of ions including, but not limited to, acylium, sulfonium, sulfurylium and phosphonium; X and Y can be H, Cl, Br, I or other leaving groups including but not limited to mesylates, tosylates and phenoxides; both X and Y can be identical or different and "n" is an integer ranging from 4 to 800 and more preferably from 65 to 800 i.e. a PEG molecular weight ranging from 3 000 to 35 000 Da.; and Q can be part of, but is not limited to, the group consisting of —$SO_2$—, —$CO(CHR_1)_tSO_2$—, —CO—, —$SO_2(CHR_1)_t$ $SO_2$—, —$SO_2$—O—$(CHR_1)_t$—O—$SO_2$, >PO, —CO—O—$(CHR_1)_t$—$CR_2$=$CR_3$—$(CHR_4)_t$—O—CO—, and —$SO_2$—O—$(CHR_1)_t$—$CR_2$=$CR_3$—$(CHR_4)_t$—O—$SO_2$—, wherein "t" is an integer ranging from 1 to 3 and wherein $R_1$, $R_2$, $R_3$ and $R_4$ are either identical or different and are selected from the group consisting of hydrogen, lower alkyl, lower branched alkyl, aryl and aralkyl. More preferably, $R_1$, $R_2$, $R_3$ and $R_4$ are selected from the group consisting of hydrogen, methyl, ethyl, isopropyl and propyl. More preferably, Q can be part of, but is not limited to, the group consisting of —$SO_2$—, —CO—O—$CH_2$—CH=CH—$CH_2$—O—CO—, $COCH_2SO_2$—, —CO—, and —$SO_2CH_2CH_2SO_2$—.

More specifically, Q may be represented by the following general Formula 1:

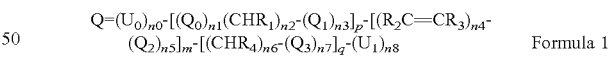

Formula 1 wherein $Q_0$, $Q_1$, $Q_2$, and $Q_3$ are identical or different, and are selected from the group consisting of oxygen and sulfur atoms; $R_1$, $R_2$, $R_3$, and $R_4$ are identical or different and are selected from the group consisting of hydrogen atom, lower alkyl, lower branched alkyl, aryl and aralkyl; $n_1$, $n_3$, $n_5$ and $n_7$ are integers selected such that $0 \leq n_1 \leq 1$, $0 \leq n_3 \leq 1$, $0 \leq n_5 \leq 1$, and $0 \leq n_7 \leq 1$; $U_0$ and $U_1$ are identical or different, and are selected from the group consisting of —CO—; —$SO_2$—, and >P=O; $n_0$ and $n_8$ are selected such that $0 \leq n_0 \leq 1$, $0 \leq n_8 \leq 1$; $n_2$, $n_4$ and $n_6$ are integers selected such that $0 \leq n_2 \leq 3$, $0 \leq n_4 \leq 1$, and $0 \leq n_6 \leq 3$; and wherein p m and q are integers selected such that $0 \leq p \leq 6$, $0 \leq m \leq 2$, $0 \leq q \leq 6$, and $0 \leq p+m \leq 8$.

Selected examples of preferred activators (Y-Q-X) include, but are not limited to the following:

EXAMPLE 1

Cl—CO—O-Ph-NO$_2$ wherein, based on Formula 1 ($n_0$=1; $n_1$=$n_2$=$n_3$=$n_8$=0; p=1; m=q=0), Q=U$_0$=—CO— and wherein X=Cl and Y=—OPh-NO$_2$ (4-nitrophenoxy).

EXAMPLE 2

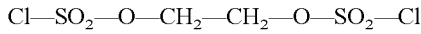
Cl—SO$_2$—O—CH$_2$—CH$_2$—O—SO$_2$—Cl wherein, based on Formula 1 ($n_0$=$n_1$=$n_3$=$n_8$=1; $n_2$=2; p=1; m=q=0; U$_0$=U$_1$=SO$_2$; Q$_0$=Q$_1$=O (oxygen); R$_1$=H), Q=-SO$_2$—O—CH$_2$—CH$_2$—O—SO$_2$— and wherein X=Y=Cl.

EXAMPLE 3

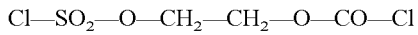
Cl—SO$_2$—O—CH$_2$—CH$_2$—O—CO—Cl wherein, based on Formula 1 ($n_0$=$n_1$=$n_2$=$n_6$=$n_7$=$n_8$=1; $n_3$=0; p=q=1; m=0; U$_0$=SO$_2$; U$_1$=—CO—; Q$_0$=Q$_3$=O (oxygen); R$_1$=R$_4$=H), Q=-SO$_2$—O—CH$_2$—CH$_2$—O—CO— and wherein X=Y=Cl.

EXAMPLE 4

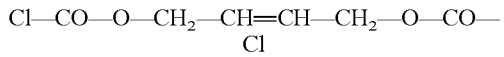
Cl—CO—O—CH$_2$—CH=CH—CH$_2$—O—CO—Cl wherein, based on Formula 1 ($n_0$=$n_1$=$n_2$=$n_4$=$n_6$=$n_7$=$n_8$=1; $n_3$=$n_5$=0; p=m=q=1; U$_0$=U$_1$=—CO—; Q$_0$=Q$_3$=O (oxygen); R$_1$=R$_2$=R$_3$=R$_4$=H), Q=—CO—O—CH$_2$—CH=CH—CH$_2$—O—CO— and wherein X=Y=Cl.

Other examples of activators include but are not limited to the following: ClSO$_2$Cl, ClCOCH$_2$SO$_2$Cl, 2-O$_2$NPhOCOCl, PhOCOCl POCl$_3$, PhOPOCl$_2$, PhPOCl$_2$, CCl$_3$COCl, CBr$_3$COCl, and Z$_b$PhOCOCl wherein Z is selected from the group consisting of Cl, Br, I, and —CN, and wherein "b" is an integer ranging from 1 to 3.

The activation process can be carried out in the presence of an aromatic nitrogen containing heterocyclic base having the general structure shown below in Formula 2:

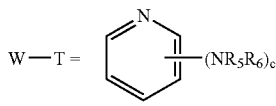
W—T = (NR$_5$R$_6$)$_c$

The NR$_5$R$_6$ substituent can be either in the ortho or para position (2- or 4-position) and R$_5$ and R$_6$ are identical or different and are selected from the group consisting of a lower straight alkyl chain, a lower branched alkyl chain, an aryl group and an aralkyl group, and wherein "c" is an integer equal to either 0, 1 or 2. R$_5$ or R$_6$ can also constitute a solid support similar to those used in peptide synthesis. More specifically, R$_5$ or R$_6$ is a solid support selected from the group consisting of amino methyl resin, p-alkoxybenzyl alcohol resin, benzhydrylamine resin, hydroxymethyl resin, 4-hydroxymethyl-benzoyloxymethyl resin, Merrifield resin, Sasrin resin, 4-methyl-benzhydrylamine resin. Additionally R$_5$ or R$_6$ can also be a solid support composed of polystyrene-divinylbenzene. Preferably, R$_5$ and R$_6$ are selected from the group consisting of methyl, ethyl, propyl, isopropyl and benzyl.

The aromatic nitrogen-containing heterocyclic base, as defined above in Formula 2, is not used (a=0), when M in the PEG entity is an atom selected from the group consisting of Li, Na, K, Rb, and Cs. It can also be used as a catalyst (0.01≦a≦1.5) at reaction temperatures ranging from about 20 to about 30° C., more preferably at room temperature, in mixtures comprising stoichiometric quantities of a tertiary amine base, selected from the group consisting of TEA, TIA, DIEA and 4-methyl morpholine.

In accordance with the present invention, there is therefore provided an activated PEG having the general structure as depicted in Formula 3:

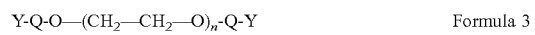
Y-Q-O—(CH$_2$—CH$_2$—O)$_n$-Q-Y    Formula 3 wherein Q is selected from, but not limited to, the group consisting of —SO$_2$—, —COCH$_2$SO$_2$—, —SO$_2$CH$_2$CH$_2$SO$_2$—; —CO—O—CH$_2$—CH=CH—CH$_2$—O—CO— and —CO—; Y is selected from, but not limited to, the group consisting of Cl and 4-O$_2$NPhO—; and wherein "n" is an integer ranging from 4 to 800 i.e. a PEG having a molecular weight from 200 to 35 000 Da.

In one preferred embodiment of the present invention, there is provided an activated PEG as described by Formula 4, wherein Y is Cl, Q is —SO$_2$— and "n" is an integer ranging from 4 to 800 I.e. a PEG having a molecular weight from 200 to 35 000 Da. Preferably, at least one embodiment is represented by the structure in Formula 4:

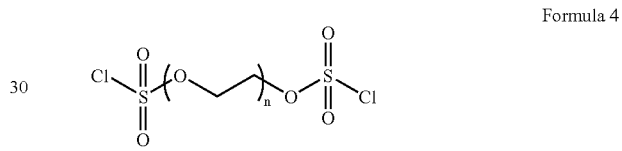

Formula 4

In another preferred embodiment of the present invention, there is provided an activated PEG as described by Formula 5, wherein Y is Cl, Q is —COCH$_2$SO$_2$— and "n" is an integer ranging from 4 to 800 i.e. a PEG having a molecular weight from 200 to 35 000 Da. Preferably, at least one embodiment is represented by the structure in Formula 5:

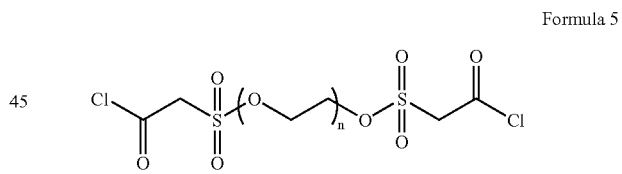

Formula 5

In yet another preferred embodiment of the present invention, there is provided an activated PEG as described by Formula 6, wherein Y is Cl, Q is —SO$_2$CH$_2$CH$_2$SO$_2$— and "n" is an integer ranging from 4 to 800 i.e. a PEG having a molecular weight from 200 to 35 000 Da. Preferably, at least one embodiment is represented by the structure in Formula 6:

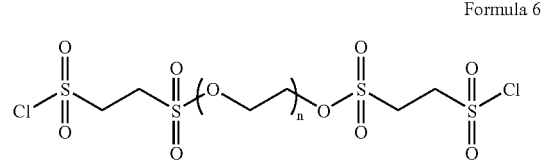

Formula 6

In still another preferred embodiment of the present invention, there is provided an activated PEG as described by Formula 7, wherein Y is 4-O$_2$NPhO—, Q is —CO— and "n" is an integer ranging from 4 to 800 i.e. a PEG having a molecular weight from 200 to 35 000 Da. Preferably, at least one embodiment is represented by the structure in Formula 7:

Formula 7

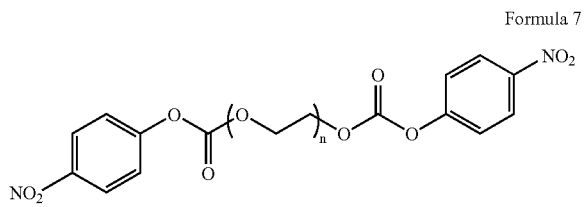

The activated polyethylene glycols are susceptible of reacting with functional groups selected from the group consisting of hydroxyl groups, amine groups and thiol groups, resulting in the formation of bio-polymers. The functional groups are derived from peptides, proteins, saccharides, polysaccharides, and oligonucleotides. The bio-polymers are used in chemical, food, cosmetical, cosmeceutical, pharmaceutical and dermopharmaceutical applications.

One preferred activation process using 4-DMAP and 4-nitrophenylchloroformate is adequately described by the reaction sequence shown below in Scheme 1:

perature under stoichiometric conditions, to produce the activated PEG in only 2 hours of reaction time. The secondary function of 4-DMAP is to act as an acid scavenger, that is, to form a salt by complexing with the hydrochloric acid (HCl) produced in the activation reaction. The scavenging of HCl by 4-DMAP is an important step in the reaction sequence, since the presence of HCl could lead to a great number of unwanted side reactions which, in turn, will have a detrimental effect on the overall efficiency of the activation reaction.

The activation of PEG using a tertiary amine base such as triethylamine (TEA) was also investigated under identical reaction conditions as those employed in the DMAP process ie. at room temperature over a period of 2 hours, and compared with the DMAP activation process. It was observed that even though 4-nitrophenyl chloroformate was again chosen as the activating reagent, the activation process required the use of a 3-fold excess of TEA and could no longer be performed at room temperature. Activation of PEG was achieved by refluxing the reaction mixture in acetonitrile (80° C.) over a period of 8 hours.

The activation of PEGs using TEA is less attractive than the process using DMAP because of the requirement for

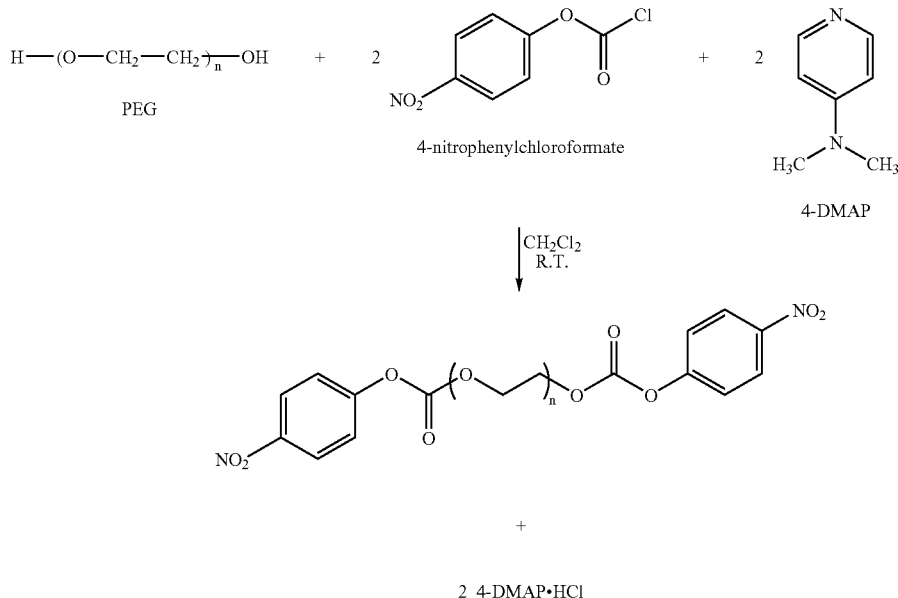

The role of 4-nitrophenyl chloroformate is to readily react with the PEG substrate, resulting in an activated PEG that can be further employed, for example, in reactions with enzyme surfaces. It was selected as the activating agent mainly because of its propensity to minimize side reactions.

The primary function of 4-DMAP is to aid in the activation process. It is assumed that it rapidly provides for a more reactive intermediate, believed to be an acylium ion, by reacting with 4-nitrophenyl chloroformate. This fleeting acylium intermediate then readily reacts with PEG in the course of an activation reaction taking place at room temrefluxing, which necessitates constant supervision. Additionally, refluxing procedures inherently require additional materials, such as reflux condensers or a soxhlet set-up. When the activation reactions are carried out on a larger scale, this additional glassware can rapidly become unwieldy and very expensive. The additional energy requirement is also a factor that cannot be ignored.

Another preferred activation process utilizing sodium PEGylate and 4-nitrophenylchloroformate is adequately described by the reaction sequence shown below in Scheme 2:

Scheme 2

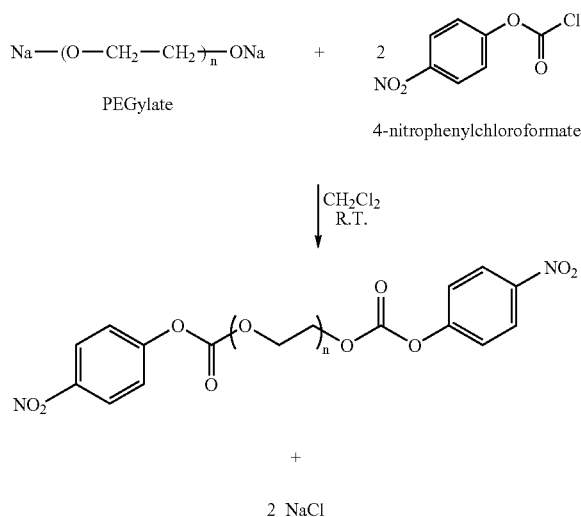

The activation process is easily carried out by first preparing the sodium PEGylate, and then reacting the PEGylate with 4-nitrophenylchloroformate.

The use of excess reagents has repercussions on the isolation and purification steps of the activation process, since these reagents will have to be removed from the activated PEG product. The reaction mixture, upon completion of the TEA-induced activation process, is mainly composed of activated PEG, unreacted TEA and 4-nitrophenyl chloroformate, as well as the hydrochloric acid (HCl) salt of TEA. In previously described processes, the isolation of the activated PEG product required several precipitation or crystallization steps before a relatively pure product was obtained. A direct comparison between the DMAP, the TEA and the sodium PEGylate activation procedures is shown in Table 1.

TABLE 1

Direct comparison of the DMAP, the TEA, and the PEGylate induced activation process.

| Comparative elements | DMAP procedure | TEA procedure | PEGylate procedure |
|---|---|---|---|
| Nitrogen base | DMAP (4-DMAP) | TEA | No nitrogen base |
| Structure | Pyridine family | Tertiary amine | NA |
| Reaction set-up | Beaker with stirrer | Reflux or soxhlet set-up | Beaker with stirrer |
| Activator | 4-Nitrophenyl chloroformate | 4-Nitrophenyl chloroformate | 4-Nitrophenyl chloroformate |
| Amount of reagents | Stoichiometric | 3-fold excess (both base and activator) | Stoichiometric |
| Solvent | $CH_2Cl_2$ | $CH_3CN$ | $CH_2Cl_2$ |
| Reaction time | 2 hours | 8 hours | 2 hours |
| Reaction temperature | 21° C. | 80° C. | 29° C. |
| Purification | Extraction and precipitation | Several precipitation/ recrystallization steps | Extraction and precipitation |
| Side products | 4-DMAP.HCl | TEA.HCl Excess TEA and activator | NaCl |
| Yield | 95% | 99% (including excess reagents) | 97% |

The crude yield of the activation reaction was calculated using Equation 2, as shown below:

$$\% \text{ Crude Yield} = \frac{\text{Amount of Crude Product (g)}}{\text{Theoretical amount of Activated PEG (g)}} \times 100\% \quad \text{Equation 2}$$

Note that the amount of crude product theoretically includes traces of non-activated PEG, mono-activated PEG and di-activated PEG (desired product). In the case of the TEA promoted activation reactions, the crude product is additionally mixed with non-negligible amounts of TEA.HCl as well as unreacted 4-nitrophenyl chloroformate, which could not be completely removed during the recrystallization/precipitation steps.

The degree of activation was calculated using Equation 3, as shown below:

$$\% \text{ Activation} = \frac{\text{Amount of p-nitrophenol generated by hydrolysis (g)}}{\text{Theoretical amount of p-nitrophenol (g)}} \times 100\% \quad \text{Equation 3}$$

Note that the amount of p-nitrophenol generated stems from the hydrolysis of the crude reaction product. The theoretical amount of p-nitrophenol expected is calculated based on the assumption that a 100% conversion of PEG into di-activated PEG has taken place.

Activation levels in excess of 100%, as are observed in the TEA-prompted activation reactions, can be explained by the persistent presence of unreacted excess 4-nitrophenyl chloroformate in the crude reaction product. This unreacted starting material will also produce 4-nitrophenol upon hydrolysis, and hence will add to the amount of 4-nitrophenol produced from the hydrolysis of the crude reaction product composed of unreacted PEG, mono-activated PEG and the desired di-activated PEG. Note that the presence of 4-nitrophenol, being a relatively strong organic acid, will result in aqueous solutions having low pH values.

The very high yields observed for the TEA activation reactions are due to difficulties incurred in the purification process. TEA.HCl, as well as excess p-nitrophenyl chloroformate, are difficult to remove entirely from the reaction mixtures. Even though an extensive precipitation/recrystallization was performed to remove these impurities from the crude reaction product, non-negligible amounts persist. Moreover this extensive precipitation/recrystallization process usually results in a significant decrease in the yield of activated PEG Some physical and chemical properties of the activated PEGs produced by the DMAP and TEA processes respectively, are provided in Table 2 below:

TABLE 2

Comparison of some physical and chemical properties of the PEGs produced by the DMAP and TEA procedure.

| Properties | DMAP procedure | TEA procedure |
|---|---|---|
| Solubility | >800 mg/ml | Whatever the concentration, a precipitate is usually observed* |
| Melting point | 53–55° C. | 54–55° C. |
| Coloration | White solid Yellow solution (deionized water) | White solid Limpid solution (deionized water) |

TABLE 2-continued

Comparison of some physical and chemical properties of the PEGs produced by the DMAP and TEA procedure.

| Properties | DMAP procedure | TEA procedure |
|---|---|---|
| pH (220 mg/ml $H_2O$) | Solution takes the pH of deionized water (pH = 5.5) | Acidic pH = 2–3 (in deionized water) |

*The precipitate is composed mainly of unreacted 4-nitrophenyl chloroformate.

The activated PEGs produced by the DMAP procedure exhibit very good water solubility, with values exceeding 800 mg/ml.

The solubility in deionized water of the PEGs activated by the TEA process, could not be determined accurately because of the appearance of a precipitate during the dissolution of the crude product. The precipitate is composed mainly of unreacted 4-nitrophenyl chloroformate which could not be entirely removed from the crude reaction product during the precipitation/recrystallization steps. Additionally, the presence of TEA.HCl in the crude reaction mixture will cause a phenomenon described as "salting out". This phenomenon causes a portion of the product itself to become insoluble in deionized water and results in it precipitating out of the solution.

The crude product generated from the TEA-promoted activation process, isolated following repeated precipitation/recrystallization steps, is essentially composed of activated PEG but contains small amounts of the hydrochloric acid salt of TEA (TEA.HCl) and unreacted p-nitrophenyl chloroformate. It is assumed that a non-negligible amount of the hydrochloric acid salt of TEA and unreacted p-nitrophenyl chloroformate remains trapped within the extensive network that constitutes activated PEG, and is consequently co-dissolved within this network.

Activated PEGs produced by the DMAP process generate aqueous solutions that adopt the pH of the solvent and that have no discernible precipitate formation. This is a direct indication of the high purity of the activated PEGs and confirms the absence of any DMAP hydrochloric acid salt (DMAP.HCl) which, in turn, is reflective of the efficiency of the purification and isolation steps of the process.

Crude activated PEGs produced by the TEA process generate substantially acidic aqueous solutions with pH values ranging between 2 and 3. This was to be expected in light of the possibility that the crude activated PEG product remains in the presence of 4-nitrophenyl chloroformate, which could not be entirely removed by the precipitation/recrystallization steps. When the crude activated PEG product produced by the TEA procedure is dissolved in water, a portion of the persistent 4-nitrophenyl chloroformate is hydrolyzed into the strong organic acid 4-nitrophenol with the concomitant formation of HCl, which brings forth the observed acidic pH values.

A comparative study of the efficiency of the DMAP and TEA processes was carried out at room temperature in $CH_2Cl_2$, using stoichiometric conditions. As is shown in Table 3, the DMAP activation process results in considerably higher activation levels over identical time intervals.

TABLE 3

Activation levels of crude PEG resulting from the DMAP and TEA processes as a function of time.
Degree of Activation*

| Reaction time (min) | DMAP mediated activation | TEA mediated activation |
|---|---|---|
| 30 | 60.0% | 32.0% |
| 60 | 59.9% | 34.5% |
| 90 | 76.9% | 31.7% |
| 120 | 97.7% | 31.3% |

*Both the DMAP and TEA reagents were used at room temperature in $CH_2Cl_2$ under stoichiometric conditions, using 4-nitrophenyl chloroformate as the activator.

As becomes readily apparent from the results depicted in Table 3, the DMAP mediated activation process is considerably more efficient than the TEA mediated process. Essentially, the entire PEG is activated within 2 hours of starting the activation reactions, whereas approximately only 30% of the PEG is activated using the TEA mediated process.

The use of stoichiometric quantities of reagents greatly simplifies the purification step. Additionally, the use of a stoichiometric amount of 4-nitrophenyl chloroformate assures that essentially all of the remaining non-reacted reagent is hydrolyzed during the extraction and precipitation steps, and will therefore not influence the quality of the final product.

The activation reactions were carried out for a given time and then stopped. The crude reaction mixtures were purified by repeated extraction and precipitation steps, and the product so-obtained was analyzed. To do this, a series of reactions were run over a 30, 60, 90 and a 120 minute period, using in one case DMAP and in another case TEA. The resulting products were subsequently analyzed for their degree of activation.

The results of another efficiency study, comparing the yields of activated PEG obtained using the DMAP and TEA processes, are shown in Table 4.

TABLE 4

Yield of crude activated PEG obtained with the DMAP and TEA processes as a function of time.
Yield(%)*

| Reaction time (min) | DMAP mediated activation process | TEA mediated activation process |
|---|---|---|
| 30 | 57.8 | 78.9 |
| 60 | 95.8 | 87.7 |
| 90 | 87.5 | 83.2 |
| 120 | 93.3 | 80.8 |

*Both the DMAP and TEA reagents were used at room temperature in $CH_2Cl_2$ under stoichiometric conditions, using 4-nitrophenyl chloroformate as the activator.

As can be observed from Table 4, relatively similar yields are obtained for both activation procedures. The lower yield observed for the DMAP procedure, as a result of a 30 minute reaction, is due to a loss of crude product incurred during the extraction/precipitation steps. However, the isolated yields obtained for the TEA process are misleading, due to the previously mentioned difficulties in effectively removing all of the unreacted 4-nitrophenyl chloroformate from the crude activated PEG product. The amount of crude activated PEG isolated from the TEA activation process contains persistent, non-negligible amounts of unreacted 4-nitrophenyl chloroformate, thus resulting in the observed higher yields. The presence of unreacted 4-nitrophenyl chloroformate is a reflection of a less efficient activation process when TEA is used. The activation process using DMAP is significantly more efficient and results in an essentially complete consumption of the 4-nitrophenyl chloroformate activating reagent. The only significant side product produced when using DMAP is its corresponding hydrochloric acid salt. This side product however, is efficiently removed from the crude activated PEG product by the extraction/precipitation steps.

The activation reactions were again carried out at room temperature in $CH_2Cl_2$ using stoichiometric conditions. A series of reactions were run for 30, 60, 90 and 120 minutes, using in one case DMAP and in another case TEA, and were then analyzed for the amount of activated PEG produced.

The propensity of the activated PEGs produced by the TEA and DMAP processes towards gelification was subsequently investigated, and the results are shown in Table 5. A gelification index of zero is indicative of a gel remaining in a liquid state whereas a gelification index of one is indicative of a slightly viscous-liquid gel (remains in an essentially liquid state). Furthermore, a gelification index of two is indicative of a gelatinous gel that is very elastic and sticky, whereas an index of three is indicative of a soft gel that is slightly sticky and slightly elastic, and that reclaims its original form upon deformation. A gelification index of four describes a rigid and non-sticky gel that also reclaims its original form upon deformation. A gelification index of four represents the desired physical state for such applications as hydrogel formation. Finally, a gelification index of five is indicative of a gum-like gel. The activated PEGs were subjected to the gelification conditions in a test tube over a 1-hour period.

TABLE 5

Gelification of crude activated PEG.
Gelification level

| DMAP mediated activation process | TEA mediated activated process | Time(min) |
|---|---|---|
| 3 | 0 | 30 |
| 3 | 0 | 60 |
| 4 | 0 | 90 |
| 4 | 0 | 120 |

Gelification could not be observed for any of the activated PEGs produced by the TEA mediated activation process. The solutions containing activated PEG resulting from a 30, 60, 90 or a 120 minute activation reaction using TEA, did not display any discernable gelification and remained essentially in a liquid state. The absence of any perceptible gelification is a direct result of a low degree of activation of the crude activated PEGs produced by the TEA mediated activation process.

Gelification was observed for all of the activated PEGs produced by the DMAP process. The solutions containing activated PEG generated from a 30, 60, 90 or a 120 minute activation reaction using DMAP resulted in the formation of gels ranging from soft to rigid. Activated PEGs produced from a 30 or 60 minute reaction result in the formation of soft gels that are slightly sticky and slightly elastic and that reclaim their original form upon deformation. Activated PEGs produced from a 90 or a 120 minute reaction result in the formation of rigid gels that are non-sticky and that also reclaim their original form upon deformation. Furthermore, these gels have the desired physical state for such applications as hydrogel preparation. The improved physical state of the gels resulting from extended reaction times, is a direct consequence of an increased degree of activation.

The melting points of the activated PEGs are an indication of their degree of activation. As can be seen from Table 6, the activated PEGs produced by the DMAP procedure have melting points that are consistently lower than those produced by the TEA procedure.

TABLE 6

Melting points of activated PEGs produced by the DMAP and TEA activation process.
Melting points ranges(° C.)

| DMAP procedure | TEA procedure | Time(min) |
|---|---|---|
| 57–59 | 60–61 | 30 |
| 57–59 | 59–61 | 60 |
| 56–57 | 59–60 | 90 |
| 53–55 | 60–61 | 120 |

The melting point for non-activated PEG ranges between about 62–63° C. Since the melting points observed for activated PEGs produced via the TEA activation process are only slightly lower, this would be an indication of their physical similarity, in turn implying a low degree of activation. In the case of the TEA activation process, the melting point observed for an activated PEG produced following a 30 minute activation reaction is identical to a PEG produced following a 120 minute activation reaction. This is in accordance with the results described in Table 3, which indicate a low degree of activation following a 30 minute reaction, with little or no change following a 120 minute reaction.

The melting points observed for activated PEGs produced via the DMAP activation process are lower than those produced by the TEA process, which is indicative of a higher degree of activation. The activated PEGs produced following a 120 minute activation reaction using the DMAP process have a lower melting point than those produced following a 30 minute activation reaction. The lower melting point is an indication of an increased degree of activation over longer reaction times. Again, these results are corroborated by the results reported in Table 3, illustrating increased activation in going from a 30 minute to a 120 minute activation reaction.

The present Invention provides for a process for the rapid activation of PEG. The activation process is conveniently carried out at room temperature over a period of 2 hours, while in the presence of stoichiometric amounts of reagents. The activated PEGs of the present invention can be used to generate hydrogels by combining them with alkaline hydrolyzed soya solutions. The activated PEGs can also be used as linkers for resins, and they can be readily linked to proteins or reacted with enzyme surfaces.

Experimental

1. Gelification Procedure a) Preparation of an 8 KDa Activated PEG [PEG-(NPC)$^2$] Solution: (220 mg/mL).

Activated PEG (8 KDa) is removed from the refrigerator and is allowed to slowly warm up to room temperature, after which 1.65 g is dissolved in deionized water (4 mL, pH=5.5) while stirring. The solution is stirred until complete dissolution is observed. If necessary, depending on the swelling of the activated PEG, the volume of deionized water is adjusted to 7.5 mL. Aliquots (500 µL) are then added to a series of test tubes.

b) Preparation of a Hydrolyzed Soya Solution: (120 mg/mL).

Hydrolyzed soya is removed from the refrigerator and is allowed to slowly warm to room temperature, after which 600 mg are placed in each of 5 test tubes (15 mL). As depicted in Table 7 below, a NaOH solution (5 mL), having a different normality, is then added to each test tube. The resulting solutions are stirred until complete dissolution is observed.

TABLE 7

Preparation of hydrolyzed soya solutions using NaOH solutions of different normality.

| Amount of hydrolyzed soya(mg) | NaOH Normality(N) | NaOH Volume(mL) |
|---|---|---|
| 600 | 0.11 | 5 |
| 600 | 0.12 | 5 |
| 600 | 0.13 | 5 |
| 600 | 0.14 | 5 |
| 600 | 0.15 | 5 | c) Hydrogel Formation: Coupling Activated PEG [PEG-(NPC)$^2$] to Hydrolyzed Soya.

A hydrolyzed soya solution (500 µL) of a given normality is pipetted and a chronometer is started. At t=10 sec, the hydrolyzed soya solution is added to a test tube containing an activated PEG solution (500 µL), prepared as previously described, while stirring using a vortex. The test tube containing the combined solution is then placed on its side so as to allow for hydrogel formation. This experiment is repeated two more times using the same hydrolyzed soya solution.

The same procedure is carried out for each of the previously described hydrolyzed soya solutions.

2. Preparation of an Activated PEG Using SO$_2$Cl$_2$

The following is an example of a general experimental process for the preparation of an activated PEG using sulfuryl chloride as the activating agent.

The reaction is carried at room temperature over a 2 hour period, in anhydrous dichloromethane (CH$_2$Cl$_2$).

Anhydrous SO$_2$Cl$_2$ (1.565 µL; 97% solution) is diluted in anhydrous CH$_2$Cl$_2$ (25 mL). The diluted sulfuryl chloride solution is then transferred to a round-bottomed flask (500 mL) and cooled in an ice bath while stirring. To this cooled solution is then added a previously prepared DMAP solution (2.44 g of DMAP were dissolved in 5 mL of anhydrous CH$_2$Cl$_2$) while stirring is continued.

PEG 8 KDa (36.36 g) is dissolved in anhydrous CH$_2$Cl$_2$ (50 mL). The PEG solution is then slowly added to the solution containing the sulfuryl chloride and DMAP reagents, kept in the ice bath under continuous stirring. Upon completion of the addition, the ice bath is removed and the reaction mixture stirred at room temperature for an additional 2 hours.

The reaction mixture is concentrated and the resulting crude solid product is extracted and precipitated with cold diethyl ether (500 mL). The suspension is then placed in a refrigerator (−20° C.) for a period of 30 minutes. The suspension is vacuum filtered and the precipitate washed with additional diethyl ether (3×100 mL). The washed precipitate is then dried under vacuum.

3. Preparation of Sodium PEGylate

The following is an example of a general experimental process for the preparation of sodium PEGylate.

The reaction is carried at room temperature in anhydrous dichloromethane (CH$_2$Cl$_2$) using stoichiometric amounts of reagents.

NaH (0.378 g of a 60% dispersion in mineral oil) was added to a double-necked round-bottomed flask equipped with a magnetic stirrer and a condenser. A CaCl$_2$ tube was positioned on top of the condenser. The round-bottomed flask was then charged with anhydrous dichloromethane (50 ml).

PEG(-OH)$_2$ 8 kDa (36.36 g; 4.5 mmoles) was dissolved in anhydrous dichloromethane (50 mL) and the resulting solution was then added dropwise under vigorous stirring to the NaH suspension. The reaction mixture was continued to be stirred until no more hydrogen gas evolution could be observed, after which it was stirred for an additional hour.

The reaction mixture was filtered or centrifuged, and the resulting dichloromethane solution was concentrated. The resulting crude product was treated with anhydrous diethyl ether (100 mL), resulting in the precipitation of PEG(-ONa)$_2$. The resulting precipitate was washed with additional portions of diethyl ether (3×100 mL) and dried under vacuum, allowing for the isolation of PEG(-ONa)$_2$ as a white solid (35.8 g; 97% yield).

4. Preparation of Activated Sodium PEGylate

The following is an example of a general experimental process for the preparation of activated sodium PEGylate.

The reaction is carried at 29° C. over a 2 hour period, in anhydrous dichloromethane (CH$_2$Cl$_2$).

Anhydrous SO$_2$Cl$_2$ (2.348 mL) is diluted in anhydrous CH$_2$Cl$_2$ (25 mL). The diluted sulfuryl chloride solution is then transferred to a double-necked round-bottomed flask (50 mL) equipped with a magnetic stirrer and a condenser. A CaCl$_2$ tube was positioned on top of the condenser. The solution was slowly heated to 29° C., and the temperature was continued to be closely monitored.

PEG(-ONa)$_2$ 8 kDa (36.36 g; 4.5 mmoles) was dissolved in anhydrous dichloromethane (50 mL) and the resulting solution was then added dropwise under vigorous stirring to the SO$_2$Cl$_2$ solution. The reaction mixture was continued to be stirred for an additional 2 hours at 29° C.

The reaction mixture was precipitated using 5 volumes of diethyl ether cooled to 4° C. The resulting suspension was then placed in a refrigerator (−20° C.) for a period of 30 minutes. The suspension is vacuum filtered and the precipitate washed with additional cold diethyl ether (3×75 mL). The washed precipitate was then recrystallized in a dichloromethane/diethyl ether solvent system.

5. Preparation of an Activated PEG Using p-nitrophenyl Chloroformate

The following is an example of a general experimental process for the preparation of an activated PEG using p-nitrophenyl chloroformate as the activating agent.

The reaction is carried at room temperature over a 2 hour period, in anhydrous dichloromethane (CH$_2$Cl$_2$).

PEG 8 KDa (363.36 g; 45 mmoles) was dissolved in anhydrous CH$_2$Cl$_2$ (500 mL), and p-nitrophenyl chloroformate (19.63 g) was dissolved in anhydrous CH$_2$Cl$_2$ (50 mL). Both solutions were then added to a reaction vessel (8.0 L) and stirred vigorously for about one 1 minute. To this solution was then added a previously prepared DMAP solution (12.22 g of DMAP were dissolved in 50 mL of anhydrous CH$_2$Cl$_2$) while stirring is continued. The reaction mixture was then stirred for an additional 2 hours at room temperature.

The reaction mixture was concentrated and precipitated using diethyl ether (2.0 L) cooled to 4° C. The resulting suspension was then placed in a refrigerator (−20° C.) for a period of 30 minutes. The suspension is vacuum filtered and the precipitate washed several times with additional cold diethyl ether. The washed precipitate was then suspended in water, stirred vigorously for about 30 minutes, and vacuum filtered. The so-obtained yellow-like filtrate was then extracted (3×) with dichloromethane and the combined solvent fractions filtered over Na$_2$SO$_4$. The filtrate was concentrated and the resulting product was precipitated under vigorous stirring using cold diethyl ether. The so-obtained PEG(NPC)$^2$ was then filtered, washed with diethyl ether, and dried under vacuum.

The terms and descriptions used herein are preferred embodiments set forth by way of illustration only, and are not intended as limitations on the many variations which those of skill in the art will recognize to be possible in practicing the present invention.

References

1. Mehvar, R.; *J. Pharm. Pharmaceut. Sci.* 2000, 3(1), 125.
2. Beauchamp, C. O.; Gonias, S. H.; Menapace, D. P.; Pizzo, S. V.; *Anal. Biochem.* 1983, 131, 25.
3. Nashimura, H.; Takahashi, K.; Sakurai, K.; Fujinuma, Y.; Imamura, Y.; Ooba, M.; Inada, Y. *Life Sci.* 1983, 33, 1467.
4. Delgado, C.; Patel, J. N.; Francis, G. E.; Fisher, D. *Biotechnol. Appl. Biochem.* 1990, 12, 119.
5. Wirth, P.; Souppe, J.; Trisch, D.; Biellmann, J.-F. *Bioorg. Chem.* 1991, 19, 133.
6. Veronese, F. M.; Largajolli, R.; Boccu, E.; Benassi, C. A.; Schiavon, O. *Appl. Biochem. Biotechnol.* 1985, 11, 141.
7. Sartore, L.; Caliceti, P.; Schiavon, O.; Veronese, F. M. *Appl. Biochem. Biotechnol.* 1991, 27, 45.
8. Anderson, W. L.; Tomasi, T. B. *J. Immunol Methods* 1988, 109, 37.
9. Zalipsky, S.; Barany, G. *J. Bioact. Comnpat. Polym.* 1990, 5, 227.
10. Fortier, G. F.; Laliberté, M. *Biotechnol. Appl. Biochem.* 1993, 17, 115.

The invention claimed is:

1. A process for preparing a bis-activated polyethylene glycol having the formula:

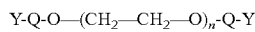

wherein
n is an integer between 4 and 800;
Y is selected from the group consisting of a halide group, a mesyl group, a tosyl group, an imidazolyl group, an N-hydroxy-succinimidyl group, a phenoxyl group, and a substituted phenoxyl group; and
Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$,
wherein
t is 1, 2, or 3; and
$R_1$, $R_2$, $R_3$ and $R_4$ are independently selected from the group consisting of H, a lower alkyl group, a lower branched alkyl group, an aryl group, and an aralkyl group;
the process consisting essentially of reacting under stoichiometric conditions a polyethylene glycol having the formula:

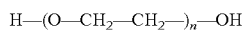

wherein
n is an integer between 4 and 800;
with an activator having the formula of Y-Q-X;
wherein
X and Y independently are selected from the group consisting of a halide group, a mesyl group, a tosyl group, an imidazolyl group, an N-hydroxy-succinimidyl group, a phenoxyl group, and a substituted phenoxy group; and
Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$,
wherein
t is 1, 2, or 3; and
$R_1$, $R_2$, $R_3$, and $R_4$ are independently selected from the group consisting of H, a lower alkyl group, a lower branched alkyl group, an aryl group, and an aralkyl group;
in the presence of a solvent and an aromatic nitrogen-containing heterocyclic base having the formula:

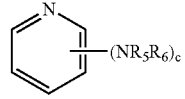

wherein
$(NR_5R_6)_c$ is located either in the ortho or para position;
$R_5$ and $R_6$ are independently selected from the group consisting of a lower straight alkyl group, a lower branched alkyl group, an aryl group, and an aralkyl group; and
c is 1 or 2;
to produce said bis-activated polyethylene glycol.

2. The process of claim 1, wherein the activator is selected from the group consisting of $Cl-CO-O-Ph-NO_2$, $Cl-SO_2-O-CH_2-CH_2-O-SO_2-Cl$, $Cl-SO_2-O-CH_2-CH_2-O-CO-Cl$, and $Cl-CO-O-CH_2-CH=CH-CH_2-O-CO-Cl$.

3. The process of claim 1, wherein said process is carried out at temperatures ranging from about 20° C. to about 30° C.

4. The process of claim 1, wherein the aromatic nitrogen-containing heterocyclic base is 4-dimethylaminopyridine.

5. The process of claim 4, wherein reacting the polyethylene glycol with the activator is in the presence of six molar equivalents or less of 4-dimethylaminopyridine.

6. A process for preparing a bis-activated polyethylene glycol having the formula:

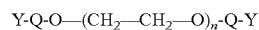

wherein
n is an integer between 4 and 800;
Y is selected from the group consisting of a halide group, a mesyl group, a tosyl group, an imidazolyl group, an N-hydroxy-succinimidyl group, a phenoxyl group, and a substituted phenoxyl group; and
Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$,
wherein
t is 1, 2, or 3; and
$R_1$, $R_2$, $R_3$ and $R_4$ are independently selected from the group consisting of H, a lower alkyl group, a lower branched alkyl group, an aryl group, and an aralkyl group;
the process consisting essentially of reacting a polyethylene glycol having the formula:

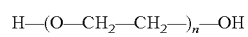

wherein
n is an integer between 4 and 800;
with an activator having the formula of Y-Q-X;

wherein
X and Y are different and independently selected from the group consisting of a halide group, a mesyl group, a tosyl group, an imidazolyl group, an N-hydroxy-succinimidyl group, a phenoxyl group, and a substituted phenoxyl group; and Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$, wherein
t is 1, 2, or 3; and
$R_1$, $R_2$, $R_3$, and $R_4$ are independently selected from the group consisting of H, a lower alkyl group, a lower branched alkyl group, an aryl group, and an aralkyl group;

in the presence of a solvent and an aromatic nitrogen-containing heterocyclic base having the formula:

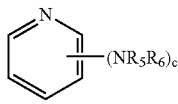

wherein
$(NR_5R_6)_c$ is located either in the ortho or para position;
$R_5$ and $R_6$ are independently selected from the group consisting of a lower straight alkyl group, a lower branched alkyl group, an aryl group, and an aralkyl group; and
c is 1 or 2;

to produce said bis-activated polyethylene glycol.

7. The process of claim 6, wherein the activator is 4-nitrophenyl chloroformate.

8. The process of claim 6, wherein the aromatic nitrogen-containing heterocyclic base is 4-dimethylaminopyridine.

9. The process of claim 6, wherein reacting the polyethylene glycol with the activator is under stoichiometric conditions.

10. The process of claim 6, wherein at least one of X and Y is a halide group.

11. The process of claim 9, wherein at least one of X and Y is a halide group.

12. A process for preparing a bis-activated polyethylene glycol having the formula:

Y-Q-O—(CH$_2$—CH$_2$—O)$_n$-Q-Y wherein
n is an integer between 4 and 800;
Y is selected from the group consisting of a halide group, a mesyl group, a tosyl group, an imidazolyl group, an N-hydroxy-succinimidyl group, a phenoxyl group, and a substituted phenoxyl group; and Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$, wherein
t is 1, 2, or 3; and
$R_1$, $R_2$, $R_3$ and $R_4$ are independently selected from the group consisting of H, a lower alkyl group, a lower branched alkyl group, an aryl group, and an aralkyl group;

the process consisting essentially of reacting a polyethylene glycol having the formula:

H—(O—CH$_2$—CH$_2$—)$_n$—OH wherein
n is an integer between 4 and 800;
with an activator having the formula of Y-Q-X;
wherein
X and Y independently are selected from the group consisting of a halide group, a mesyl group, a tosyl group, an imidazolyl group, an N-hydroxy-succinimidyl group, a phenoxyl group, and a substituted phenoxyl group, provided that at least one of X and Y is a halide group; and Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$, wherein
t is 1, 2, or 3; and
$R_1$, $R_2$, $R_3$, and $R_4$ are independently selected from the group consisting of H, a lower alkyl group, a lower branched alkyl group, an aryl group, and an aralkyl group;

in the presence of a solvent and an aromatic nitrogen-containing heterocyclic base having the formula:

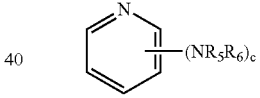

wherein
$(NR_5R_6)_c$ is located either in the ortho or para position;
$R_5$ and $R_6$ are independently selected from the group consisting of a lower straight alkyl group, a lower branched alkyl group, an aryl group, and an aralkyl group; and
c is 1 or 2;

to produce said bis-activated polyethylene glycol.

13. The process of claim 12, wherein the activator is selected from the group consisting of Cl—CO—O-Ph-NO$_2$, Cl—SO$_2$—O—CH$_2$—CH$_2$—O—SO$_2$—Cl, Cl—SO$_2$—O—CH$_2$—CH$_2$—O—CO—Cl, and Cl—CO—O—CH$_2$—CH=CH—CH$_2$—O—CO—Cl.

14. The process of claim 12, wherein the aromatic nitrogen-containing heterocyclic base is 4-dimethylaminopyridine.

15. The process of claim 12, wherein reacting the polyethylene glycol with the activator is under stoichiometric conditions.

16. The process of claim 12, wherein reacting the polyethylene glycol with the activator is at room temperature.

17. The process of claim 16, wherein X and Y are different.

18. A process for preparing a bis-activated polyethylene glycol having the formula:

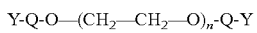

wherein
n is an integer between 4 and 800;
Y is selected from the group consisting of a halide group, a mesyl group, a tosyl group, an imidazolyl group, an N-hydroxy-succinimidyl group, a phenoxyl group, and a substituted phenoxyl group; and
Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$,
wherein
t is 1, 2, or 3; and
$R_1$, $R_2$, $R_3$ and $R_4$ are independently selected from the group consisting of H, a lower alkyl group, a lower branched alkyl group, an aryl group, and an aralkyl group;
the process consisting essentially of reacting a polyethylene glycol having the formula:

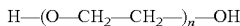

wherein
n is an integer between 4 and 800;
with an activator having the formula of Y-Q-X;
wherein
X and Y independently are selected from the group consisting of a halide group, a mesyl group, a tosyl group, an imidazolyl group, an N-hydroxy-succinimidyl group, a phenoxyl group, and a substituted phenoxyl group; and
Q is selected from the group consisting of $SO_2$, $CO(CHR_1)_tSO_2$, $CO-O-(CHR_1)_t-O-SO_2$, $C(O)$, $SO_2(CHR_1)_tSO_2$, $SO_2-O-(CHR_1)_t-O-SO_2$, $CO-O-(CHR_1)_t-CR_2=CR_3-(CHR_4)_t-O-CO$, and $SO_2-O-(CHR_1)_t-CR_2=CR_3-(CHR_4)_t-O-SO_2$, wherein
t is 1, 2, or 3; and
$R_1$, $R_2$, $R_3$, and $R_4$ are independently selected from the group consisting of H, a lower alkyl group, a lower branched alkyl group, an aryl group, and an aralkyl group;
at a temperature range between about 20° C. and about 30° C., and in the presence of a solvent and an aromatic nitrogen-containing heterocyclic base having the formula:

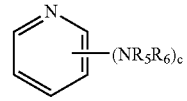

wherein
$(NR_5R_6)_c$ is located either in the ortho or para position;
$R_5$ and $R_6$ are independently selected from the group consisting of a lower straight alkyl group, a lower branched alkyl group, an aryl group, and an aralkyl group; and
c is 1 or 2;
to produce said bis-activated polyethylene glycol.

19. The process of claim 18, wherein the activator is selected from the group consisting of $Cl-CO-O-Ph-NO_2$, $Cl-SO_2-O-CH_2-CH_2-O-SO_2-Cl$, $Cl-SO_2-O-CH_2-CH_2-O-CO-Cl$, and $Cl-CO-O-CH_2-CH=CH-CH_2-O-CO-Cl$.

20. The process of claim 18, wherein the aromatic nitrogen-containing heterocyclic base is 4-dimethylaminopyridine.

21. The process of claim 18, wherein X and Y are different.

22. The process of claim 21, wherein reacting the polyethylene glycol with the activator is under stoichiometric conditions.

23. The process of claim 22, wherein at least one of X and Y is a halide group.

* * * * *